US00PP15780P2

(12) United States Plant Patent
Lin

(10) Patent No.: US PP15,780 P2
(45) Date of Patent: May 31, 2005

(54) ***PENTAS* PLANT NAMED 'BISMARCK PINK'**

(50) Latin Name: *Pentas lanceolata*
Varietal Denomination: Bismarck Pink

(75) Inventor: Soru Lin, Taipai (TW)

(73) Assignee: John Bodger & Sons Company, South El Monte, CA (US)

( * ) Notice: Subject to any disclaimer, the term of this patent is extended or adjusted under 35 U.S.C. 154(b) by 0 days.

(21) Appl. No.: 10/822,989

(22) Filed: Apr. 13, 2004

(51) Int. Cl.[7] ..... A01H 5/00

(52) U.S. Cl. ..... Plt./263

(58) Field of Search ..... Plt./263

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Pentas* plant named 'Bismarck Pink', characterized by its upright and somewhat outwardly spreading plant habit; short internodes and freely branching habit; dense and bushy growth habit; small, dark green-colored leaves; freely flowering habit; and large pink-colored flowers with white-colored throats arranged in large terminal corymbs that are positioned above the foliage.

1 Drawing Sheet

Botanical classification/cultivar designation: *Pentas lanceolata* cultivar Bismarck Pink.

BACKGROUND OF THE INVENTION

The present Invention relates to a new and distinct cultivar of *Pentas* plant, botanically known as *Pentas lanceolata*, and hereinafter referred to by the name 'Bismarck Pink'.

The new *Pentas* is a product of a planned breeding program conducted by the Inventor in Pintung, Taiwan. The objective of the breeding program was to develop new moderately tall and freely branching *Pentas* cultivars with numerous large flowers and attractive flower and foliage coloration.

The new *Pentas* originated from a cross-pollination made by the Inventor during the summer of 1995 of two unidentified proprietary selections of *Pentas lanceolata*, not patented. The cultivar Bismarck Pink was discovered and selected by the Inventor as a flowering plant within the progeny of the stated cross-pollination in a controlled environment in Pintung, Taiwan in 1996.

Asexual reproduction of the new cultivar by terminal cuttings in Pintung, Taiwan, since the summer of 1996, has shown that the unique features of this new *Pentas* are stable and reproduced true to type in successive generations of asexual reproduction.

SUMMARY OF THE INVENTION

The following traits have been repeatedly observed and are determined to be the unique characteristics of 'Bismarck Pink'. These characteristics in combination distinguish 'Bismarck Pink' as a new and distinct *Pentas* cultivar:

1. Upright and somewhat outwardly spreading plant habit.
2. Short internodes and freely branching habit; dense and bushy growth habit.
3. Small, dark green-colored leaves.
4. Freely flowering habit.
5. Large pink-colored flowers with white-colored throats arranged in large terminal corymbs that are positioned above the foliage.

Plants of the new *Pentas* differ primarily from plants of the parent selections in the following characteristics:

1. Plants of the new *Pentas* are taller than plants of the parent selections.
2. Plants of the new *Pentas* have larger inflorescences with larger flowers than plants of the parent selections.

The new *Pentas* can be compared to the *Pentas lanceolata* cultivar Butterfly, not patented. However, in side-by-side comparisons conducted in Pintung, Taiwan, plants of the new *Pentas* differed from plants of the cultivar Butterfly in the following characteristics:

1. Plants of the new *Pentas* had smaller, more rugose and darker green-colored leaves than plants of the cultivar Butterfly.
2. Plants of the new *Pentas* had larger flowers with thicker petals than plants of the cultivar Butterfly.
3. Flowers of plants of the new *Pentas* were longer lasting than flowers of plants of the cultivar Butterfly.
4. Plants of the new *Pentas* did not set seed whereas plants of the cultivar Butterfly set seed.

The new *Pentas* can also be compared to the *Pentas lanceolata* cultivar New Look Graffiti, not patented. However, in side-by-side comparisons conducted in Pintung, Taiwan, plants of the new *Pentas* differed from plants of the cultivar New Look Graffiti in the following characteristics:

1. Plants of the new *Pentas* were taller and more vigorous than plants of the cultivar New Look Graffiti.
2. Plants of the new *Pentas* had smaller and darker-green colored leaves than plants of the cultivar New Look Graffiti.
3. Plants of the new *Pentas* had larger inflorescences and larger flowers than plants of the cultivar New Look Graffiti.
4. Flowers of plants of the new *Pentas* were longer lasting than flowers of than plants of the cultivar New Look Graffiti.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Pentas*.

The photograph at the bottom of the sheet comprises a side perspective view of a flowering plant of 'Bismarck Pink' grown in a container.

The photograph at the top of the sheet is close-up view of typical flowers and leaves of 'Bismarck Pink'.

DETAILED BOTANICAL DESCRIPTION

Plants of the cultivar Bismarck Pink have not been observed under all possible environmental consitions. The phenotype may vary somewhat with variations in environment such as temperature and light intensity, without, however, any variance in genotype. The aforementioned photographs and following observations and measurements describe plants grown in Lompoc, Calif., under commercial practice in a polycarbonate-covered greenhouse during the winter. During the production of the plants, day temperatures ranged from 21 to 30° C., night temperatures ranged from 16 to 18° C. and light levels ranged from 5,000 to 9,000 foot-candles. Rooted young plants were pinched once and then planted in 15.25-cm containers. Plants had been growing for about 31 weeks when the photographs and the description were taken. In the following description, color references are made to The Royal Horticultural Society Colour Chart, 1995 Edition, except where general terms of ordinary dictionary significance are used.

Botanical classification: *Pentas lanceolata* cultivar Bismarck Pink.

Parentage:

*Female, or seed, parent.*—Unidentified proprietary selection of *Pentas lanceolata*, not patented.

*Male, or pollen, parent.*—Unidentified proprietary selection of *Pentas lanceolata*, not patented.

Propagation:

*Type cutting.*—Terminal cuttings.

*Time to initiate roots, summer.*—About 9 to 10 days at 30 to 32° C.

*Time to initiate roots, winter.*—About 10 to 12 days at 20 to 25° C.

*Time to produce a rooted young plant, summer.*—About 20 to 25 days at 28 to 32° C.

*Time to produce a rooted young plant, winter.*—About 28 to 30 days at 20 to 25° C.

*Root description.*—Fine, fibrous; white in color.

*Rooting habit.*—Dense; moderately branching.

Plant description:

*General appearance.*—Upright and somewhat outwardly spreading plant habit; narrow inverted triangle.

*Growth and branching habit.*—Vigorous and freely-branching growth habit with about eight lateral branches per plant; short internodes, dense and bushy growth habit. Pinching, that is removal of the terminal apex, enhances branching potential.

*Plant height.*—About 26 cm.

*Plant diameter or spread.*—About 28 cm.

*Lateral branches.*—Length: About 20 cm. Diameter: About 6 mm. Internode length: About 3.8 cm. Texture: Pubescent. Strength: Strong. Color: 144A.

*Foliage description.*—Arrangement: Opposite, simple. Length: About 8.5 cm. Width: About 5.2 cm. Shape: Elliptical. Apex: Acute. Base: Acute to attenuate. Margin: Entire. Texture, upper and lower surfaces: Pubescent; coarse; rugose. Venation pattern: Pinnate; arcuate. Color: Developing and fully expanded foliage, upper surface: 147A. Developing and fully expanded foliage, lower surface: 147B. Venation, upper surface: 144A. Venation, lower surface: 147C. Petiole: Length: About 3 cm. Diameter: About 3 mm. Texture, upper and lower surfaces: Pubescent; tough. Color: 144B.

Flower description:

*Flower type and habit.*—Numerous, large, salverform, star-shaped, single flowers that are arranged on large terminal hemispherical corymbs; about 62 flowers and about 30 flower buds per corymb. Flowers face upright and outward. Inflorescences positioned above the foliage on erect peduncles. Flowers last about 7 to 10 days under greenhouse conditions. Flowers not persistent. Flowers not fragrant.

*Natural flowering season.*—In the garden, flowering is continuous through the spring and summer. In the greenhouse, flowering is continuous year-round.

*Inflorescence height.*—About 4.2 cm.

*Inflorescence diameter.*—About 8.5 cm.

*Flower height.*—About 2 cm.

*Flower diameter.*—About 2.8 cm.

*Flower tube length.*—About 2.5 cm.

*Flower throat diameter.*—About 4 mm.

*Flower tube diameter.*—About 2 mm.

*Flower buds.*—Length: About 1.8 cm. Diameter: Towards the apex, about 3 mm; towards the base, about 1.5 mm. Shape: Elongated ovoid. Color: 182C.

*Petals.*—Quantity per flower/arrangement: Five in a single whorl; fused at base. Lobe length: About 1 cm. Lobe diameter: About 6 mm. Lobe shape: Elliptic. Lobe apex: Acute. Lobe base: Fused. Lobe margin: Entire. Texture, upper and lower surfaces: Smooth, glabrous; velvety. Color: When opening, upper surface: 68A. When opening, lower surface: 73B. Fully opened, upper surface: 68B to 68C. Fully opened, lower surface: 73B to 73C. Throat: 155D. Tube: 73A to 73B.

*Sepals.*—Quantity per flower/arrangement: Five in a single whorl; fused at base. Length: About 4 to 8 mm. Width: About 1 to 2 mm. Shape: Elliptic. Apex: Acute. Base: Fused. Margin: Entire. Texture, upper and lower surfaces: Smooth, glabrous. Color, upper surface: 147A. Color, lower surface: 147B.

*Peduncles.*—Length: About 1.8 cm. Diameter: About 3 mm. Angle: Upright to about 45° from vertical. Strength: Strong. Texture: Smooth. Color: 144A.

*Pedicels.*—Length: About 3 mm. Diameter: About 1.5 mm. Angle: Upright to about 45° from vertical. Strength: Strong. Texture: Smooth. Color: 147C.

*Reproductive organs.*—Stamens: Quantity per flower: Five. Anther size: About 1 mm by 3 mm. Anther shape: Oblong. Anther color: 70D. Pollen amount: Scarce. Pollen color: 155C. Pistils: Quantity per flower: One. Pistil length: About 2.7 cm. Stigma shape: Two-parted. Stigma color: 155D. Style length: About 2 cm. Style color: 155A. Ovary color: 145C.

*Seed/fruit.*—Seed and fruit production have not been observed.

Disease/pest resistance: Plants of the new *Pentas* have been observed to be resistant to Pythium, Rhizoctonia and Botrytis. Plants of the new *Pentas* have not been observed to be resistant to other pathogens and pests common to *Pentas*.

Temperature tolerance: Plants of the new *Pentas* have been observed to tolerate temperatures from 10 to 35° C.

It is claimed:

1. A new and distinct cultivar of *Pentas* plant named 'Bismarck Pink', as illustrated and described.

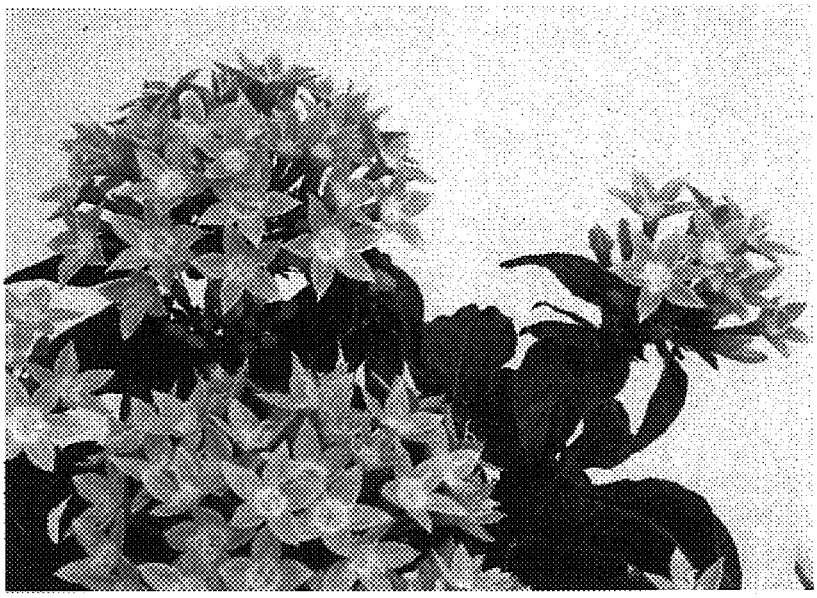
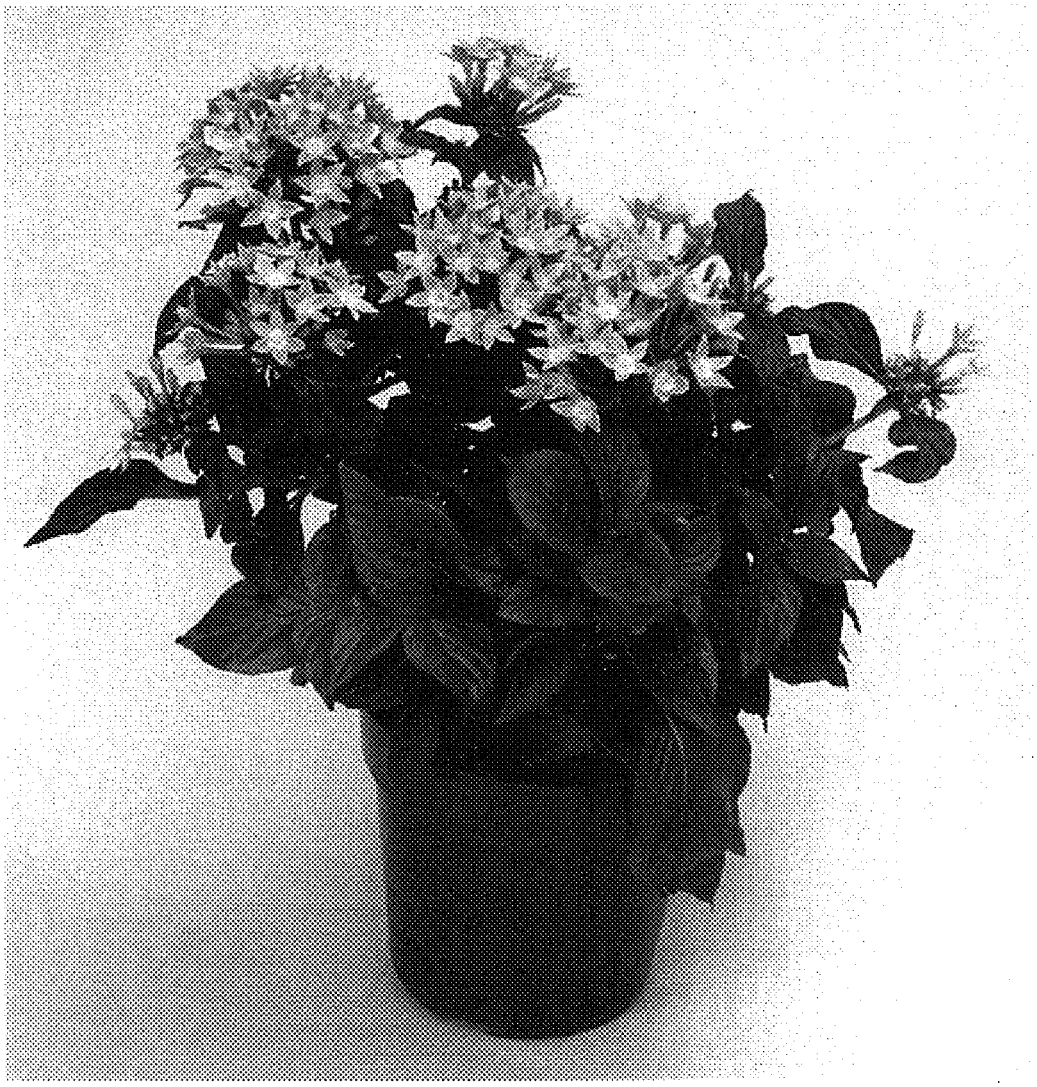

* * * * *